(12) United States Patent
Michel et al.

(10) Patent No.: US 7,309,558 B1
(45) Date of Patent: Dec. 18, 2007

(54) USE OF SALT-LIKE STRUCTURED SILICAS AS CHARGE CONTROL AGENTS

(75) Inventors: Eduard Michel, Frankfurt am Main (DE); Rüdiger Baur, Eppstein-Niederjosbach (DE); Hans-Tobias Macholdt, Darmstadt-Eberstadt (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 0 days.

(21) Appl. No.: 09/722,760

(22) Filed: Nov. 27, 2000

(30) Foreign Application Priority Data

Nov. 27, 1999 (DE) .............................. 199 57 245

(51) Int. Cl.
G03G 9/097 (2006.01)

(52) U.S. Cl. ............................. 430/137.1; 430/108.21; 430/108.24; 307/400

(58) Field of Classification Search ........... 430/108.24, 430/108.3, 108.7, 108.1, 108.21, 137.1; 307/400
See application file for complete search history.

(56) References Cited

U.S. PATENT DOCUMENTS

| | | | | |
|---|---|---|---|---|
| 3,925,278 A | * | 12/1975 | Murai et al. ................. | 106/240 |
| 4,054,537 A | | 10/1977 | Wright et al. ................ | 252/317 |
| 4,404,270 A | | 9/1983 | Higashida et al. .......... | 430/465 |
| 4,808,849 A | | 2/1989 | Inculet et al. | |
| 4,912,006 A | | 3/1990 | Breitschaft et al. | |
| 4,992,262 A | * | 2/1991 | Nakagaki et al. ............. | 424/63 |
| 5,015,676 A | | 5/1991 | Macholdt et al. ........... | 523/453 |
| 5,021,473 A | | 6/1991 | Macholdt et al. ........... | 523/451 |
| 5,043,239 A | | 8/1991 | Kukimoto ................... | 430/126 |
| 5,051,585 A | | 9/1991 | Koshishiba et al. ........ | 250/306 |
| 5,069,994 A | | 12/1991 | Gitzel et al. | |
| 5,147,748 A | | 9/1992 | Gitzel et al. | |
| 5,342,723 A | | 8/1994 | Macholdt et al. | |
| 5,378,571 A | | 1/1995 | Macholdt et al. | |
| 5,385,776 A | * | 1/1995 | Maxfield et al. ............ | 428/297 |
| 5,401,809 A | | 3/1995 | Gitzel et al. ................. | 525/337 |
| 5,475,119 A | | 12/1995 | Baur et al. ................... | 548/570 |
| 5,502,118 A | | 3/1996 | Macholdt et al. ........... | 525/437 |
| 5,556,618 A | | 9/1996 | Ando et al. ............... | 424/78.08 |
| 5,585,216 A | | 12/1996 | Baur et al. | |
| 5,807,629 A | * | 9/1998 | Elspass et al. .............. | 428/323 |
| 5,871,845 A | | 2/1999 | Dahringer et al. .......... | 428/378 |
| 6,030,738 A | * | 2/2000 | Michel et al. ........... | 430/108.22 |

FOREIGN PATENT DOCUMENTS

| | | | |
|---|---|---|---|
| CA | 2244367 | * | 1/1999 |
| DE | 27 18 576 | | 11/1977 |
| DE | 31 20 542 | | 3/1982 |
| DE | 39 33 166 | | 5/1990 |
| DE | 40 29 652 | | 3/1992 |
| DE | 40 31 705 | | 4/1992 |
| DE | 42 42 541 | | 6/1993 |
| DE | 43 21 289 | | 1/1995 |
| DE | 43 32 170 | | 3/1995 |
| DE | 44 18 842 | | 12/1995 |
| EP | 0 385 580 | | 4/1990 |
| EP | 0 258 651 | | 11/1993 |
| EP | 0 575 805 | | 12/1993 |
| EP | 0 347 695 | | 4/1994 |
| EP | 0 636 945 | | 2/1995 |
| EP | 0 778 501 | | 6/1997 |
| JP | 55-166652 | * | 12/1980 |
| JP | 8-6295 | * | 1/1996 |
| WO | WO 91/10172 | | 7/1991 |

OTHER PUBLICATIONS

Grant, R. et al. ed. Grant & Hackh's Chemical Dictionary, Fifth Edition, McGraw-Hill Book Co., N Y (1987), pp. 22, 23, 71, 321, and 434.*
Americal Chemical Society (ACS) File Registry No. RN 1332-58-7, copyright 2002.*
Japanese Patent Office English-Language Abstract of JP 55-166652 (Pub Dec. 25, 1980).*
Japanese Patent Office Machine-Assisted Translation of JP 8-6295 (Pub Jan. 1996).*
Thomson-Derwent Machine-Assisted Translation of JP 8-6295 (Pub Jan. 1996).*
PCT Search Report.
Abstract for JP Publication No. 08006295.
Abstract for JP Publication No. 02221964.
Abstract for JP Patent No. 2217867 (XP-002159326).
Abstract for JP Patent No. 7181719 (XP-002159327).
Abstract for JP Publication No. 60066262.
Abstract for JP Patent No. 2299878 (XP-002159328).
English abstract for JP 5163449, Jun. 29, 1993.
Y. Higashiyama, et al., *J. Electrostatics*, 30, pp. 203-212, 1993.
A. Singewald, et al., *Zeitschrift fur Physikal. Chem.*, vol. 124, 223-248, 1981.
U.S. Patent Application No. 11/596,639 by Michel et al., filed Nov 14, 2006.

* cited by examiner

*Primary Examiner*—Janis L. Dote
(74) *Attorney, Agent, or Firm*—Anthony A. Bisulca

(57) ABSTRACT

The present invention relates to the use of salt-like structured silicates, in which the cation is $NH_4^+$, $H_3O^+$, an alkali metal, alkaline earth metal, earth metal or transition metal ion or a low molecular weight organic cation or a combination thereof and the anion is an island, cyclic, group, chain, ribbon, laminar or matrix silicate or a combination thereof as charge control agents in electrophotographic toners and developers, in powder coatings, electret materials and in electrostatic separation processes.

6 Claims, No Drawings

USE OF SALT-LIKE STRUCTURED SILICAS AS CHARGE CONTROL AGENTS

CROSS-REFERENCE TO RELATED APPLICATIONS

The present invention is described in the German priority application No. DE 19957245.3, filed 27 Nov. 1999, which is hereby incorporated by reference as is fully disclosed herein.

BACKGROUND OF THE INVENTION

Field of the Invention

The present invention relates to the field of charge control agents in the sense of a component which selectively influences the electrostatic charging properties in a matrix.

In electrophotographic recording processes a "latent charge image" is produced on a photoconductor. The "latent charge image" is developed by application of an electrostatically charged toner, which is then transferred, for example, to paper, textiles, films or plastic and is fixed, for example by means of pressure, radiation, heat or the action of solvents. Typical toners are one- of two-component powder toners (also called one- or two-component developers), and special toners, such as, for example, magnetic toners, liquid toners or polymerization toners, are furthermore also in use. Polymerization toners are to be understood as meaning those toners which are formed, for example, by suspension polymerization (condensation) or emulsion polymerization and lead to improved particle properties of the toner. The term furthermore also means those toners which in principle are produced in nonaqueous dispersions.

A measure of the toner quality is its specific charging q/m (charge per unit weight). In addition to the symbol and level of the electrostatic charging, an important quality criterion is the rapid achievement of the desired level of charge, the constancy of this charge over a relatively long activation period and the insensitivity of the toner toward climatic influences, such as temperature and atmospheric humidity. Both positively and negatively chargeable toners are used in copiers and laser printers, depending on the type of process and apparatus. To obtain electrophotographic toners or developers with either positive or negative charging, charge control agents are frequently added. Since toner binders often show a marked dependency of the charging on the activation time, the task of a charge control agent is on the one hand to establish a symbol and level of the toner charging and on the other hand to counteract the charging drift of the toner binder and ensure constancy of the toner charging. Moreover, it is important in practice for the charge control agent to have an adequate heat stability and a good dispersibility. Typical incorporation temperatures for charge control agents in the toner resins are between 100° C. and 200° C. using kneaders or extruders. A heat stability of 200° C. is accordingly of great advantage. It is also important that the heat stability is guaranteed over a relatively long period of time (about 30 minutes) and in various binder systems.

For a good dispersibility, it is advantageous that the charge control agent has no wax-like properties, no tackiness and a melting or softening point of >150° C., preferably >200° C. Tackiness frequently leads to problems in metering into the toner formulation, and low melting or softening points can mean that no homogeneous distribution is achieved on dispersing in, since the material closes together in droplet form in the carrier material.

Typical toner binders are polymerization, polyaddition and polycondensation resins, such as styrene, styrene/acrylate, styrene/butadiene, acrylate, polyester and phenol/epoxide resins, as well as cycloolefin copolymers, individually or in combination, which can also comprise further constituents, for example coloring agents, such as dyestuffs and pigments, waxes or flow auxiliaries, or to which further constituents can also subsequently be added, such as finely divided silicas.

Charge control agents can also be employed to improve the electrostatic charging of powders and coatings, in particular in powder coatings which can be sprayed triboelectrically or electrokinetically, such as are used for surface coating of objects made of, for example, metal, wood, plastic, glass, ceramic, concrete, textile material, paper or rubber. The powder coating or the powder in general acquires its electrostatic charging by one of the following two processes: In the corona process the powder coating or the powder is passed by a charged corona and charged as a result, and in the triboelectric or electrokinetic process use is made of the principle of frictional electricity. A combination of the two processes is also possible. In the spraying apparatus the powder coating or the powder acquires an electrostatic charging which is opposite to the charge of the friction partner, in general a hose or spray tube, for example made of polytetrafluoroethylene.

Epoxy resins, polyester resins containing carboxyl and hydroxyl groups and polyurethane and acrylic resins, together with the customary hardeners, are typically employed as powder coating resins. Combinations of resins are also used. Thus, for example, epoxy resins are frequently employed in combination with polyester resins containing carboxyl and hydroxyl groups.

It has furthermore been found that charge control agents can considerably improve the charging and the charge stability properties of electret materials, in particular electret fibers (DE-A-43 21 289). Typical electret materials are based on polyolefins, halogenated polyolefins, polyacrylates, polyacrylonitriles, polystyrenes or fluorine polymers, such as, for example, polyethylene, polypropylene, polytetrafluoroethylene and perfluorinated ethylene and propylene, or on polyesters, polycarbonates, polyamides, polyimides or polyether ketones, on polyarylene sulfides, in particular polyphenylenesulfides, or on polyacetals, cellulose esters or polyalkylene terephthalates, and mixtures thereof. Electret materials, in particular electret fibers, can be employed, for example, for (extra-fine) dust filtration. The electret materials can acquire their charge by corona charging or tribocharging.

Charge control agents can moreover be used in electrostatic separation operations, in particular in separation operations on polymers. For instance, Y. Higashiyama et al. (J. Electrostatics 30, pp 203-212 (1993)) describe how polymers can be separated from one another for recycling purposes by the example of the externally applied charge control agent trimethyl-phenyl-ammonium tetraphenylborate. Without charge control agents low density polyethylene (LDPE) and high density polyethylene (HDPE) charge substantially similarly by frictional electricity. After addition of charge control agents LDPE becomes highly positively charged and HDPE highly negatively charged and they can thus be easily separated. As well as external application of charge control agents, incorporation thereof into the polymer is also possible, for example in order to shift a polymer within the triboelectric voltage series and to obtain a corresponding separating effect. Other polymers, such as, for example, polypropylene (PP) and/or polyethylene terephthalate (PET) and/or polyvinyl chloride (PVC) can also be separated from one another in this manner.

Salt minerals can also be separated if an agent which improves the substrate-specific electrostatic charging (surface conditioning) has been added to them beforehand (A. Singewald et al., Zeitschrift für Physikal. Chem., Vol. 124, pp 223-248 (1981)).

Charge control agents are furthermore employed as electroconductivity providing agents (ECPA) (JP-05-163 449) in inks for ink-jet printers and for electronic inks.

A silica fine powder which has been treated with a specific polysiloxane is known from DE-A1-39 33 166 as a developer for image-producing processes. EP-A1-0 575 805 describes a charge control agent composition which is a solids mixture of a quaternary ammonium salt and an inorganic pigment, such as, for example, calcium sulfate or calcium silicate.

SUMMARY OF THE INVENTION

The object of the present invention was to discover active and ecotoxicologically tolerated charge control agents which show, in particular, a high rapid charging. They should furthermore be readily dispersible without decomposition in various toner binders appropriate in practice, such as polyesters, polystyrene/acrylates or polystyrene-butadienes/epoxide resins as well as cycloolefin copolymers. Their action should furthermore be largely independent of the resin/carrier combination, in order to open up a broad application. They should also be readily dispersible without decomposition in the usual powder coating binders and electret materials, such as, for example, polyester (PES), epoxide, PES-epoxy hybrid, polyurethane, acrylic systems and polypropylenes.

In respect of their electrostatic efficiency, the charge control agents should already be active at the lowest possible concentration (1% or less) and should not lose this efficiency in combination with carbon black or other coloring agents. It is known of coloring agents that in some cases they can influence the triboelectric charging of toners for a long time.

Surprisingly, it has now been found that salt-like structured silicates described below have advantageous charge control properties and high heat stabilities, the charge control property being lost neither by combination with carbon black nor with other coloring agents. The compounds are moreover readily compatible with the customary toner, powder coating and electret binders and can easily be dispersed. The resin-carrier systems which usually have a negative control can furthermore also be effectively charged positively. Thus, the invention, in one form, provides a method of imparting, controlling or improving the charge of an electrophotographic toner or developer, of a powder coating, of an electret material or in an electrostatic separation process.

DESCRIPTION OF THE PREFERRED EMBODIMENTS

The present invention relates to the use of salt-like structured silicates in which the cation is $NH_4^+$, $H_3O^+$, an alkali metal, alkaline earth metal, earth metal or transition metal ion or a low molecular weight organic cation or a combination thereof and the anion is an island, cyclic, group, chain, ribbon, laminar or matrix silicate or a combination thereof as a charge control agent in electrophotographic toners and developers, in powder coatings and electret materials and in electrostatic separation processes.

According to the customary definition, the structured silicates mentioned are based on the following empirical formulae:

for island silicates $[SiO_4]^{4-}$, for group silicates $[Si_2O_7]^{6-}$, for cyclic silicates $[SiO_3]_n^{2-}$, for chain silicates $[SiO_3]_m^{2-}$, for ribbon silicates $[Si_4O_{11}]_m^{6-}$, for laminar silicates $[Si_2O_5]_m^{2-}$ and for matrix silicates $[Al_aSi_{1-a}O_2]_m^{a-}$, in which n=3, 4, 6 or 8, m is an integer and is $\geq 1$ and $0<a<1$. Structured silicates are frequently accompanied by further low molecular weight anions, such as, for example, $OH^-$, $F^-$, $Cl^-$, $Br^-$, $I^-$, $BO_3^{3-}$, $BO_2(OH)^{2-}$, $BO(OH)_2^-$, $HCO_3^-$, $CO_3^{2-}$, $NO_3^-$, $HSO_4^-$, $SO_4^{2-}$, $H_2PO_4^-$, $HPO_4^{2-}$, $PO_4^{3-}$, $HS^-$ or $S^{2-}$.

Furthermore, in structured silicates some individual Si atoms can be replaced by other atoms, such as, for example, Al, B, P or Be ("aluminosilicates", "borosilicates" and the like). Naturally occurring or synthetically prepared structured silicates are furthermore distinguished in that they comprise one or more different cations, which are often easily exchangeable, such as, for example, $Na^+$, $K^+$, $Mg^{2+}$ and $Ca^{2+}$, and, for example, can be replaced by organic ions, whereupon their chemical and physical properties can change. The silicate changed in this way can be, for example, highly hydrophobized and therefore readily processable in non-polar media. In the case of laminar silicates, the individual silicate platelet is enveloped by the organic ions in this manner. These coated molecules can assemble together over their surfaces to give lamellae. If an excess of organic ions is used, these can also additionally be embedded between the lamellae.

Preferred structures silicates in the sense of the present invention are montmorillonite, bentonite, hectorite, kaolinite, serpentine, talc, pyrophyllite, mica, phlogopite, biotite, muscovite, paragonite, vermiculite, beidellite, xantophyllite, margarite, feldspar, zeolite, wollastonite, actinolite, amosite, crocidolite, sillimanite, nontronite, smectite, sepiolite, saponite, faujasite, permutite and sasil.

Examples of naturally occurring structured silicates are:

$Be_2[SiO_4]$ phenacite, forsterite $Mg_2[SiO_4]$, olivine $(Mg,Fe)_2[SiO_4]$, fayalite $Fe_2[SiO_4]$, granates $M_2^{III}M_3^{II}[SiO_4]_3$ ($M^{II}=Mg^{2+}$, $Ca^{2+}$, $Fe^{2+}$, $Mn^{2+}$, $M^{III}=Al^{3+}$, $Fe^{3+}$, $Cr^{3+}$), zirconium $Zr[SiO_4]$, thortveitite $Sc_2[Si_2O_7]$, barysilite $Pb_3[Si_2O_7]$, hemimorphite $Zn_4(OH)_2[Si_2O_7]$, α-wollastonite $Ca_3[Si_3O_9]$, benitoite $BaTi[Si_3O_9]$, beryl $Al_2Be_3[Si_6O_{18}]$, dioptase $Cu_6[Si_6O_{18}].6H_2O$, dravite $Na\{Mg_3Al_6(OH)_4(BO_3)_3[Si_6O_{18}]\}$, Schörl $Na\{Fe_3^{II}(Al,Fe^{III})_6(OH)_4(BO_3)_3[Si_6O_{18}])\}$, β-wollastonite $Ca[SiO_3]$, enstatite $Mg[SiO_3]$, diopside $CaMg[SiO_3]_2$, spodumen $LiAl[SiO_3]_2$, pyroxenes, amphiboles, tremolite $Ca_2Mg_5(OH)_2[Si_4O_{11}]_2$, anthophyllite $(Mg,Fe^{II})_7(OH)_2[Si_4O_{11}]_2$, actinolite $(Ca,Na)_2(Fe,Mg,Al)_5(OH)_2[(Si,Al)_4O_{11}]_2$, amosite $(Fe^{II}Mg,Al)_7(OH)_2[(Si,Al)_4)_{11}]_2$, crocidolite $Na_2(Fe^{II},Mg)_3(Fe^{III})_2[(Si,Al)_4O_{11}]_2$, sillimanite $Al[AlSiO_5]$, mullite, krauskopfite, rhodonite, stokesite, serpentine $Mg_3(OH)_4[Si_2O_5]$, kaolinite $Al_2(OH)_4[Si_2O_5]$, halloysite $Al_2(OH)_4[Si_2O_5].2H_2O$, kaolin, petalite $LiAl[Si_2O_5]_2$, apophyllite $Ca_4K(F)[Si_2O_5]_4$, gillespite $BaFe[Si_2O_5]_2$, anorthite $Ca_2[SiAlO_4]_4$, hexacelsian $Ba_2[SiAlO_4]_4$, talc $Mg_3(OH)_2[Si_2O_5]_2$, pyrophyllite $Al_2(OH)_2[Si_2O_5]_2$; kanemite $NaH[Si_2O_5]$;

laminar aluminosilicates: mica, phlogopite $K\{Mg_3(OH,F)_2[AlSi_3O_{10}]\}$, biotite $K\{(Mg,Fe,Mn)_3(OH,F)_2[AlSi_3O_{10}]\}$, paragonite $Na\{Al_2(OH,F)_2[AlSi_3O_{10}]\}$, muscovite $K\{Al_2(OH,F)_2[AlSi_3O_{10}]\}$, fluoromuscovite $K\{Al_2F_2[AlSi_3O_{10}]\}$, micas of the composition $(K,H_3O)_y\{Mg_3(OH)_2[Si_{4-y}Al_yO_{10}]\}$ or $(K,H_3O)_y\{Al_2(OH)_2-[Si_{4-y}Al_yO_{10}]\}$, in which y=0.7 to 0.9, brittle micas, for example xantophyllite $Ca\{Mg_3(OH)_2[Al_2Si_2O_{10}]\}$ or margarite $Ca\{Al_2(OH)_2[Al_2Si_2O_{10}]\}$, mica-like silicates, such as, for example vermiculite $(Mg(H_2O)_6.2H_2O)_{0.66}\{[Mg,Fe^{III},Al)_3(OH)_2[Al_{1.25}Si_{2.75}O_{10}]\}$, illites, montmorillonite $Na_{0.33}\{(Al_{1.67}Mg_{0.33})(OH)_2[Si_4O_{10}]\}$, bentonites, beidellite $(Ca,Na)_{0.3}\{Al_2(OH)_2[Al_{0.5}Si_{3.5}O_{10}]\}$, nontronite $Na_{0.33}\{Fe_2^{III}(OH)_2[Al_{0.33}Si_{3.67}O_{10}]\}$, sepiolite, smectites, saponite $(Ca,Na)_{0.33}\{(Mg,Fe^{II})_3(OH)_2[Al_{0.33}Si_{3.67}O_{10}]\}$, laponite or hectorite $Na_{0.33}\{(Mg,Li)_3(OH,F)_2[Si_4O_{10}]\}$, feldspars, such as, for example, $K[AlSi_3O_8]$, $Na[AlSi_3O_8]$, $Ca[Al_2Si_2O_8]$, $Na[AlSiO_4]$, $K[AlSi_2O_6]$;

matrix aluminosilicates, such as, for example zeolites, for example faujasite $Na_2Ca[Al_2Si_4O_{12}]_2.16H_2O$, chabazite $(Na_2,Ca)[Al_2Si_4O_{12}].6H_2O$, mordenite $Na_2[Al_2Si_{10}O_{24}].6H_2O$, natrolite $Na_2[Al_2Si_3O_{10}].2H_2O$, permutite, sasil, zeolite A $Na_{12}[Al_{12}Si_{12}O_{24}].27H_2O$, zeolite X $Na_{43}[Al_{43}Si_{83}O_{126}].132H_2O$, zeolite Y $Na_{28}[Al_{28}Si_{68}O_{96}].125H_2O$, and other matrix aluminosilicates, such as, for example, ultramarines or lasurite.

The ionic structured silicate can be either of natural origin, for example contained in or alongside a naturally occurring mineral or rock, such as, for example, bentonite or montmorillonite, or a synthetically prepared structured silicate, for example a magnesium hydrosilicate or a synthetic hectorite (for example DE-A-2718 576) or $Na_2[Si_2O_5]$.

In the case of a naturally occurring structured silicate, the geographical deposit can have an influence on the chemical and physical properties of the material Ionic structured silicates, which in nature are often acccompanied by other minerals or rocks (for example quartz), can be worked up by mechanical or chemical process steps, for example very finely ground, purified by or separated from other concomitant substances, pH-treated, dehydrated, pressure-treated, heat-treated or treated by oxidation or reduction or with chemical auxiliaries.

Trade names for structured silicates which can be employed for the purposes of the invention are:
TONSIL®, GRANOSIL®, SUDFLOCK®, COPISIL®, OPAZIL®, PRINTOSIL®, LIGHTCOAT®, JETSIL®, GEKO®, ECOSIL®, TIXOTON®, BENTONIL®, MONTIGEL®, CALCIGEL®, CLARIT®, LAUNDROSIL®, BIONIT®, EDASIL®, AGRIBEN®, TIXOGEL®, OPTIBENT®, OPTIGEL®, AIRSEC®, ALBION ®kaolin, BIOKAT'S®, CONTAINER DRI®, DESI PAK®, IVYBLOCK®, MONTIGEL®, DETBUILD®, BLEACH®, VOLCLAY®, BENTO-BRITE®, POLARGEL®, and SUSPENGEL®.

Structured silicates which are also used in other sectors, such as, for example, bleaching bentonite, paper bentonites, foundry bentonites, ceramic bentonites, desiccants, thickeners, antisedimentation agents, catalysts and water softening/water treatment and purification agents, can also be employed in the sense of the invention.

Possible metal cations of the structured silicates used according to the invention are for example
$Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Al^{3+}$, $TiO^{2+}$, $ZrO_{2+}$, $Zn^{2+}$, $Fe^{2+}$, $Fe^{3+}$, $Sn^{2+}$, $Sn^{4+}$, $Pb^{2+}$, $Pb^{4+}$, $Cr^{3+}$, $Mn^{4+}$, $Mn^{2+}$, $Co^{2+}$, $Co^{3+}$, $Cu^{2+}$, $Sc^{3+}$, $Ti^{4+}$, $Zr^{4+}$, $V^{5+}$, $Y^{3+}$, $Ni^{2+}$, $Mo^{6+}$ and $W^{6+}$.

The low molecular weight organic cations are preferably substituted ammonium, phosphonium, thionium or triphenylcarbonium ions or a cationic metal complex.

Preferred ions are low molecular weight, tha is to say nonpolymeric, ammonium ions of the formulae (a)-(j):

(a)

(b)

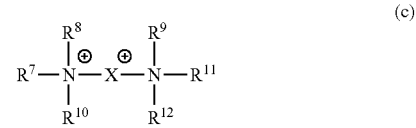

(c)

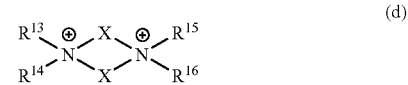

(d)

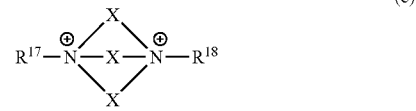

(e)

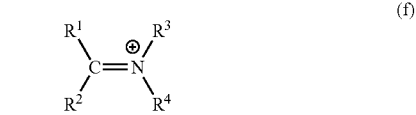

(f)

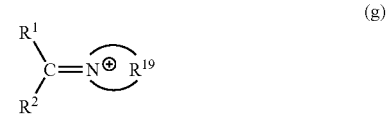

(g)

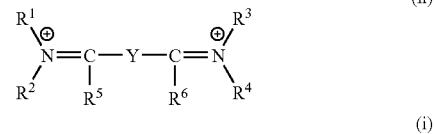

(h)

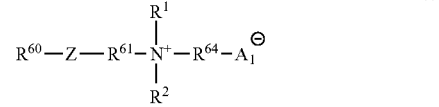

(i)

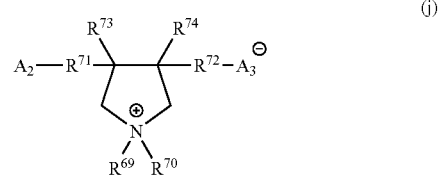

(j)

in which
$R^1$ to $R^{18}$ are identical or different and represent hydrogen, CN, $(CH_2)_{1-18}CN$, halogen, for example F, Cl or Br, branched or unbranched $C_1$-$C_{32}$-alkyl, mono- or polyunsaturated $C_2$-$C_{32}$-alkenyl, in particular $C_2$-$C_{22}$-alkenyl, such as, for example tallow fatty alkyl; $C_1$-$C_{22}$-alkoxy, $C_1$-$C_{22}$-hydroxyalkyl, $C_1$-$C_{22}$-halogenalkyl, $C_2$-$C_{22}$-halogenalkenyl, $C_1$-$C_{22}$-aminoalkyl, $(C_1$-$C_{12})$-trialkyl-ammonium-$(C_1$-$C_{22})$-alkyl;
$(C_1$-$C_{22})$-alkylene-(C=O)O—$(C_1$-$C_{32})$alkyl, $(C_1$-$C_{22})$-alkylene-(C=O)O-aryl, $(C_1$-$C_{22})$-alkylene-(C=O)NH—$(C_1$-$C_{32})$alkyl, $(C_1$-$C_{22})$-alkylene-(C=O)NH-aryl, $(C_1$-$C_{22})$-alkylene-O(C=O)—$(C_1$-$C_{32})$alkyl, in particular (C$_1$-C$_{18}$)-alkylene-O(CO)—(C$_1$-C$_{32}$)alkyl, (C$_1$-C$_{22}$)-alkylene-O(CO)aryl, (C$_1$-C$_{22}$)-alkylene-NH(C=O)—(C$_1$-C$_{32}$)alkyl, (C$_1$-C$_{22}$)-alkylene-NHCO-aryl, wherein —$[$O—(CH$_2$)$_{1-12}$$]_{1-20}$—  or  —$[$NH—(CH$_2$)$_{1-12}$$]_{1-20}$, can be inserted into the acid ester or acid amide bonds;

[(C$_1$-C$_{12}$)-alkylene-O—]$_{1-100}$—H; aryl, (C$_1$-C$_{18}$)-alkylenearyl, —(O—SiR'$_2$)$_{1-32}$—O—SiR'$_3$, in which R' has the meaning C$_1$-C$_{12}$-alkyl, phenyl, benzyl or C$_1$-C$_{12}$-alkoxy;

heterocyclyl, C$_1$-C$_{18}$-alkylene-heterocyclyl;

R$^{19}$ represents C$_4$-C$_{11}$-alkylene, —(C$_2$H$_4$—O—)$_{1-17}$—(CH$_2$)$_{1-2}$—, —(C$_2$H$_4$—NR—)$_{1-17}$—(CH$_2$)$_{1-2}$—, in which R is hydrogen or C$_1$-C$_{12}$-alkyl;

X has the meaning of Y and —CO—CH$_2$—CO—,

—$[$O—(CH$_2$)$_{1-12}$$]_{1-20}$,  —$[\overset{H}{N}$—(CH$_2$)$_{1-12}$$]_{1-20}$,

—C(=NH)—CH$_2$—C(=NH)—,

1/2 [pyrene tetraone structure],

1/2 [benzene tetraacyl structure]  or

1/2 [perylene tetraone structure];

Y has the meaning

—C(=O)—,  —C(=S)—,  —C(=NH)—,

—(CH$_2$)$_{1-18}$—,

—(CH$_2$)$_{1-12}$—HN—CO—⟨phenyl⟩—CO—NH—(CH$_2$)$_{1-12}$—,

—(CH$_2$)$_{1-12}$—O—CO—⟨phenyl⟩—CO—O—(CH$_2$)$_{1-12}$— or o-, p-, m-(C$_6$-C$_{14}$)-arylene or (C$_4$-C$_{14}$)-heteroarylene with 1, 2, 3 or 4 heteroatoms from the group consisting of N, O and/or S;

R$^{60}$ represents C$_1$-C$_{32}$-acyl, C$_1$-C$_{22}$-alkyl, C$_2$-C$_{22}$-alkenyl, C$_1$-C$_{18}$-alkylene-C$_6$-C$_{10}$-aryl, C$_1$-C$_{22}$-alkylene-heterocyclyl, C$_6$-C$_{10}$-aryl or (C$_4$-C$_{14}$)-heteroaryl with 1, 2, 3 or 4 heteroatoms from the group consisting of N, O and/or S, R$^{61}$ and R$^{64}$ represent —(CH$_2$)$_{1-18}$—, C$_1$-C$_{12}$-alkylene-C$_6$-C$_{10}$-arylene, C$_6$-C$_{10}$-arylene, C$_0$-C$_{12}$-alkylene-heterocyclyl;

Z represents —NH— or —O—;

A$_1^-$ and A$_3^-$ represent —COO$^-$, —SO$_3^-$, —OSO$_3^-$, —SO$_2^-$, —COS$^-$ or —CS$_2^-$;

A$_2$ represents —SO$_2$Na, —SO$_3$Na, —SO$_2$H, —SO$_3$H or hydrogen;

R$^{69}$ and R$^{70}$ independently of one another represent hydrogen, C$_1$-C$_{32}$-alkyl, in which the alkyl chain can contain one or more of the groups —NH—CO—, —CO—NH—, —CO—O— or —O—CO—;

C$_1$-C$_{18}$-alkylene-aryl, C$_0$-C$_{18}$-alkylene-heterocyclyl, C$_1$-C$_{18}$-hydroxyalkyl, C$_1$-C$_{18}$-halogenoalkyl, aryl, —(CH$_2$)$_3$—SO$_3^-$, —CH$_2$—CH(SO$_2^-$)—CH$_2$—SO$_3^-$,  or  —CH$_2$—CH(SO$_3^-$)—CH$_2$—SO$_3^-$;

R$^{71}$ and R$^{72}$ represent —(CH$_2$)$_{1-12}$—; and
R$^{73}$ and R$^{74}$ represent hydrogen or C$_1$-C$_{22}$-alkyl.

Unless described otherwise, "aryl" in the preceding and following definitions preferably represents C$_6$-C$_{18}$-aryl, in particular phenyl or naphthyl, "heterocycyl" preferably represents a saturated, unsaturated or aromatic, five- to seven-membered ring with 1, 2, 3 or 4 heteroatoms from the group consisting of N, O and/or S, for example pyridyl, imidazolyl, triazinyl, pyridazyl, pyrimidinyl, pyrazinyl, piperidinyl, morpholinyl, purinyl, tetrazonyl, or pyrrolyl. The aryl and heterocyclyl radicals can furthermore be mono- or polysubstituted, for example 2, 3, 4 or 5 times, on carbon atoms or heteroatoms by C$_1$-C$_{12}$-alkyl, C$_1$-C$_4$-alkenyl, C$_1$-C$_4$-alkoxy, hydroxy-(C$_1$-C$_4$)alkyl, amino-(C$_1$-C$_4$)alkyl, C$_1$-C$_4$-alkylimino, carboxyl, hydroxyl, amino, nitro, cyano, halogen, C$_1$-C$_{12}$-acyl, C$_1$-C$_4$-halogenoalkyl, C$_1$-C$_4$-alkylcarbonyl, C$_1$-C$_4$-alkylcarbonyloxy, C$_1$-C$_4$-alkoxycarbonyl, C$_1$-C$_4$-alkylaminocarbonyl, C$_1$-C$_4$-alkylcarbonylimino, C$_6$-C$_{10}$-arylcarbonyl, aminocarbonyl, aminosulfonyl, C$_1$-C$_4$-alkylaminosulfonyl, phenyl, naphthyl or heteroaryl, for example pyridyl, imidazolyl, triazinyl or pyrimidinyl.

Heterocyclic ammonium ions which are furthermore preferred are aliphatic or aromatic 5- to 12-membered heterocyclic radicals with 1, 2, 3 or 4 N, O and/or S atoms belonging to rings, it being possible for 2 to 8 rings to be fused, in particular pyridinium, pyridazinium, pyrimidinium, pyrazinium, purinium, tetraazaporphyrinium, piperidinium, morpholinium, tetrazonium triazacyclononanium or tetraazacyclododecanium. Further suitable heterocyclic radicals are, for example, pyrrolium, pyrazolium, imidazolium, benzimidazolium, imidazolonium, benzimidazolonium, imidazolinium, benzimidazolinium, alkylpyrrolidino-benzimidazolonium, indolium, isoindolium, indolizinium, pyrrolizidinium, carbazolium, indazolium, quinolinium, isoquinolinium, pyrindenium, acridinium, phenanthridinium, lilolinium, julolinium, matridinium, cinnolinium, quinazolinium, quinoxalinium, perimidinium, phenazonium, phenazinium, 1,10-phenanthrolinium, β-carbolinium, quinolizinium, 1,8-naphthyldrinium, pteridinium, quinuclidinium, conidinium, hypoxanthinium, adeninium, xanthinium, isoxanthinium, heteroxanthinium, isoadeninium, guaninium, epiquaninium, theophyllinium, paraxanthinium, theobrominium, caffeinium, isocaffeinium, trihydroxypurinium, porphyrinium, tetraazaphorphyrinium, metal-complexed tetraazaphorphyrinium (for example with Mg, Ca, Sr, Ba, Al, Mn, Fe, Co, Cu, Zr, Ti, Cr, Ni or Zn), bis-tetrazonium, phenoxazinium and aminoxanthenium, and derivatives of the cations mentioned mono- or polysubstituted on carbon atoms or heteroatoms, it being possible for the substituents to be, independently of one another, carboxyl, hydroxyl, $C_1$-$C_{22}$-alkoxy, $C_1$-$C_{32}$-alkyl, in particular $C_1$-$C_{22}$-alkyl, $C_2$-$C_{22}$-alkenyl, hydroxy-($C_1$-$C_{22}$)-alkyl, amino, aminoalkyl, $C_1$-$C_{18}$-iminoalkyl, alkylamido, alkylcarbonyloxy, alkyloxycarbonyl, ($C_1$-$C_{22}$)-alkylene-(C=O)O—($C_1$-$C_{32}$) alkyl, ($C_1$-$C_{22}$)-alkylene-(C=O)O-aryl, ($C_1$-$C_{22}$)alkylene-(C=O)NH—($C_1$-$C_{32}$)alkyl, ($C_1$-$C_{22}$)-alkylene-(C=O)NH-aryl, ($C_1$-$C_{22}$)-alkylene-O(CO)—($C_1$-$C_{32}$)alkyl, ($C_1$-$C_{22}$) alkylene-O(CO)-aryl, ($C_1$-$C_{22}$)alkylene-NH(C=O)—($C_1$-$C_{32}$)alkyl, ($C_1$-$C_{22}$)-alkylene-NHCO-aryl; wherein

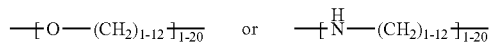

can be inserted into the acid ester or acid amide bonds;
nitro, cyano, halogen, poly($C_1$-$C_{12}$-alkylene oxide) or $C_1$-$C_{22}$-acyl, in particular N- or C—($C_1$-$C_{22}$)-alkylated heterocyclic radicals, as mentioned above, for example N—($C_1$-$C_{20}$)alkyl-pyridinium or 1-methyl-1-stearylamidoethyl-2-stearyl imidazolinium.

Ions of the formulae (a)-(j) which are of particular interest are those in which $R^1$ to $R^{18}$ denote hydrogen, CN, $CH_2$—CN, $CF_3$, $C_1$-$C_{22}$-alkyl, for example coconut alkyl, cetyl, stearyl or hydrogenated tallow fatty alkyl; $C_2$-$C_{22}$-alkenyl, in particular $C_2$-$C_{18}$-alkenyl, $C_1$-$C_{18}$-alkoxy, $C_1$-$C_{18}$-hydroxy-alkyl, $C_1$-$C_{18}$-halogenoalkyl, $C_2$-$C_{18}$-halogenoalkenyl, in which halogen preferably denotes F or Cl, $C_1$-$C_{18}$-aminoalkyl, ($C_1$-$C_6$)-trialkylammonium-($C_1$-$C_{18}$)-alkyl, ($C_1$-$C_{18}$)-alkylene-O(C=O)—($C_1$-$C_{22}$)alkyl, ($C_1$-$C_{18}$)-alkylene-O(C=O)-phenyl, ($C_1$-$C_{18}$)-alkylene-NHCO—($C_1$-$C_{22}$)alkyl, ($C_1$-$C_{18}$)-alkylene-NHCO-phenyl, ($C_1$-$C_{18}$)-alkylene-(C=O)O—($C_1$-$C_{22}$)alkyl, ($C_1$-$C_{18}$)-alkylene-(C=O)O-phenyl, ($C_1$-$C_{18}$)alkylene-(C=O)NH—($C_1$-$C_{22}$) alkyl, ($C_1$-$C_{18}$)-alkylene-CONH-phenyl, benzyl, phenyl, naphthyl or $C_1$-$C_{12}$-alkylene-heterocyclyl;
$R^{19}$ denotes $C_4$-$C_5$-alkylene, —($C_2H_4$—O$)_{1-9}$—($CH_2)_{1-2}$— or —($C_2N_4$—NH$)_{1-9}$—($CH_2)_{1-2}$—;
$R^{60}$ denotes $C_1$-$C_{18}$-acyl, $C_1$-$C_{18}$-alkyl, $C_2$-$C_{18}$-alkenyl, $C_1$-$C_{12}$-alkylene-phenyl, $C_1$-$C_{18}$-alkylenepyridyl, phenyl or pyridyl;
$R^{61}$ and $R^{64}$ denote —($CH_2)_{1-12}$—, $C_1$-$C_8$-alkylenephenylene, phenylene or $C_1$-$C_8$-alkylenepyridylene or -piperidylene;
$R^{71}$ and $R^{72}$ denote —($CH_2)_{1-8}$ and
$R^{73}$ and $R^{74}$ denote hydrogen or ($C_1$-$C_{18}$)-alkyl.

Preferred low molecular weight organic cations are furthermore cationic metal complexes, such as metal carboxylates, metal salicylates, metal sulfonates, 1:1 metal-azo complexes or metal dithiocarbamates, in which metal is preferably Al, Mg, Ca, Sr, Ba, TiO, VO, Cr, V, Ti, Zr, Sc, Mn, Fe, Co, Ni, Cu, Zn and ZrO and the metal complex optionally contains one or more further ligands.

Preferred metal carboxylate and salicylates are those of the formulae (k) and (l)

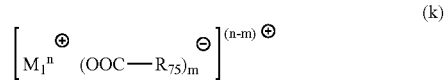

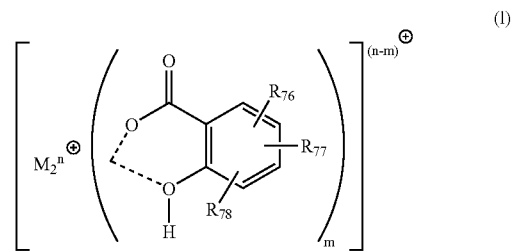

in which n=2, 3 or 4;
m=1, 2 or 3, but is always less than n;
$M_1^{np}$ and $M_2^{np}$ independently of one another are a metal cation of the main group or transitions metals, for example represent B, Al, Mg, Ca, Sr, Ba, Sc, V, Ti, Zr, TiO, Cr, Mn, Fe, Co, Ni, Cu, Zn or ZrO.
$R_{75}$ can be $C_1$-$C_{32}$-alkyl (linear or branched), $C_1$-$C_{22}$-halogenalkyl, $C_1$-$C_{18}$-hydroxyalkyl, $C_1$-$C_{18}$-aminoalkyl, $C_1$-$C_{18}$-ammoniumalkyl, $C_1$-$C_{18}$-alkylene-aryl, $C_1$-$C_{18}$-alkylene-heterocyclyl, aryl or heterocyclyl, as defined above; and
$R_{76}$ to $R_{78}$ independently of one another can be $C_1$-$C_{12}$-alkyl (linear or branched), $C_1$-$C_4$-alkoxy, hydroxyl, carboxyl, $C_1$-$C_4$-alkenyl, hydroxy-($C_1$-$C_4$)-alkyl, amino, ($C_1$-$C_4$)-aminoalkyl, nitro, cyano, halogen, $C_1$-$C_{12}$-acyl, $C_1$-$C_4$-iminoalkyl, $C_1$-$C_4$-halogenoalkyl, aryl or heterocyclyl, as defined above.

Analogous cationic complexes or salts of the abovementioned metals with ligands, such as α-hydroxyphenol, α-aminoaniline, α-hydroxyaniline, α-aminobenzoic acid, quinoline, 1,8-diaminonaphthalene, 1,4,5,8-tetraaminonaphthalene, 1,8-dihydroxynaphthalene or 1,4,5,8-tetrahydroxynaphthalene, are furthermore suitable.

Analogous cationic complexes or salts of the abovementioned metals with ligands or anions, such as, for example, α,α-dipyridyl, ethylenediamine, diethylenetriamine, triethylenetetraamine, acetylacetonate, ortho-phenanthroline, benzoyl ketones, ethylened(biguanidine), biguanidine or dimethylglyoxime, are furthermore suitable.

Preferred 1:1 metal-azo complexes are those of the formulae (m)-(p)

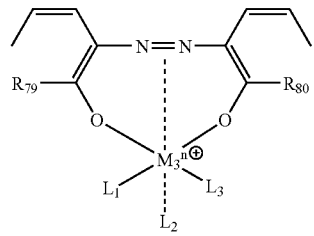 (m)

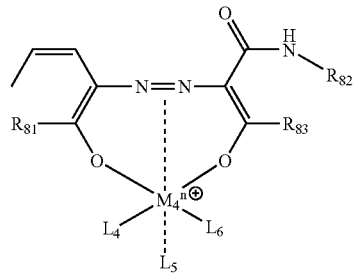 (n)

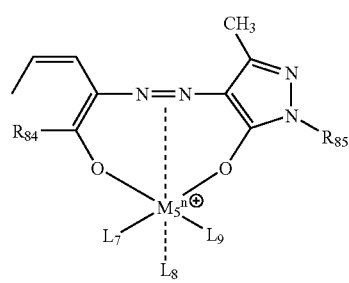 (o)

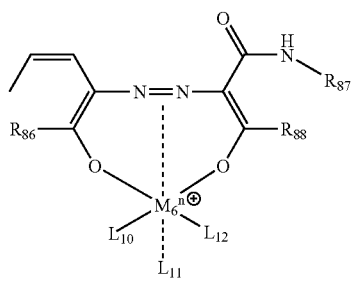 (p)

wherein $M_3^{n+}$ to $M_6^{n+}$ have one of the meanings of $M_1^{n+}$ or $M_2^{n+}$, $R_{79}$, $R_{80}$, $R_{81}$, $R_{84}$ and $R_{86}$ independently of one another are an atomic group, which are optionally carry substituents, needed to complete a mono- or dinuclear ring system of aromatic character, $R_{82}$ and $R_{87}$ independently of one another are a phenyl radical which optionally carries substituents or a ($C_1$-$C_{12}$)-alkyl or ($C_1$-$C_2$)-alkoxy-($C_2$-$C_8$)-alkyl radical, $R_{83}$, $R_{85}$ and $R_{88}$ independently of one another are $C_1$-$C_{12}$-alkyl or phenyl, optionally carrying substituents, and the ligands $L_1$ to $L_{12}$ independently of one another can be $H_2O$, $OH^-$, $NH_3$, $F^-$, $Cl^-$, $Br^-$, $I^-$, $NO_3^-$, $HSO_4^-$, $SO_4^{2-}$, $H_2PO_4^-$, $HPO_4^{2-}$, $PO_4^{3-}$, $BO_3^{3-}$, $BO_2(OH)^{2-}$, $BO(OH)_2^-$, $HCO_3^-$, $CO_3^{2-}$, $H_2S$, $HS^-$, $S^{2-}$, oxalate, citrate, formate, acetate, propionate, fumarate, maleate, tartrate, $C_1$-$C_4$-alkylsulfonate, tauride, methyltauride, sarcoside, methylsarcoside, lactate and other low molecular weight carboxylates and sulfonates.

Cationic complexes or salts which are furthermore suitable are those of the abovementioned metals with dithiocarbamate ligands according to the formula (o)

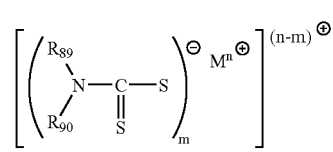 (o)

in which the radicals $R_{89}$ and $R_{90}$ independently of one another have one of the meanings of $R_1$ and m and n are a number from 1 to 4, where n>m.

Cations which are furthermore suitable are triaza-cyclononanium or tetraaza-cyclododecanium cations of the formulae (p) and (q)

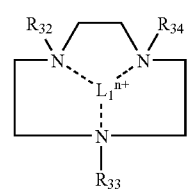 (p)

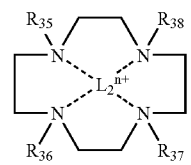 (q)

in which $R_{32}$ to $R_{38}$ independently of one another can be H, $C_1$-$C_{32}$-alkyl, $C_2$-$C_{18}$-alkenyl, $C_1$-$C_{18}$-halogenoalkyl, $C_1$-$C_{18}$-alkoxy, $C_1$-$C_{18}$-hydroxyalkyl, ($C_1$-$C_8$)alkylene-($C_6$-$C_{14}$)-aryl or ($C_1$-$C_{10}$)-alkyleneheteroaryl, for example ($C_1$-$C_{10}$)-alkylene-pyridyl, n represents a number between 1 and 4 and $L_1$ and $L_2$ and represent a low molecular weight cation, for example hydrogen or a main group or transition metal, such as Li, Na, K, Rb, Cs, Be, Mg, Ca, Sr, Ba, Al, TiO, ZrO, Mn, VO, Fe, Co, Cu, Zn, Cr, Ni, Mo or W.

Ammonium cations which are furthermore suitable are those of the general formula (r)

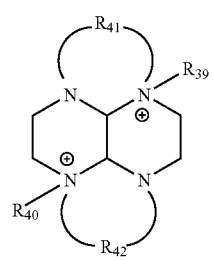 (r)

in which $R_{39}$ and $R_{40}$ independently of one another have one of the meanings of $R_{32}$; and $R_{41}$ and $R_{42}$ represent ($-CH_2-)_n$, where n=2 to 9.

Amino acids which are furthermore suitable are those of the general formula (s)

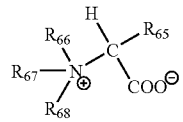
(s)

in which the radicals $R_{66}$ to $R_{68}$ independently of one another can be hydrogen, $C_1$-$C_{22}$-alkyl, $C_1$-$C_{18}$-hydroxyalkyl, $(C_1$-$C_{22})$-halogenoalkyl, $(C_1$-$C_{18})$-alkylenearyl, for example benzyl, $(C_1$-$C_{18})$-alkyleneheteroaryl, $(C_6$-$C_{10})$-aryl, heteroaryl, for example pyridyl, heterocycyl, for example morpholinyl or piperidinyl, or $(C_1$-$C_8)$-alkyleneheterocycyl and $R_{65}$ can be hydrogen, $C_1$-$C_{18}$-alkyl, $C_1$-$C_{18}$-hydroxyalkyl, $C_1$-$C_{18}$-thioalkyl, $C_1$-$C_{18}$-aminoalkyl, $C_1$-$C_{18}$-carboxyalkyl, $C_1$-$C_{18}$-alkylenearyl, for example benzyl, $C_1$-$C_{18}$-alkyleneheteroaryl, $C_1$-$C_{18}$-alkyleneheterocyclyl $C_6$-$C_{10}$-aryl, $(C_4$-$C_{10})$-heteroaryl, $(C_4$-$C_{10})$-heterocyclyl, for example morpholinyl or piperidinyl, $C_1$-$C_{22}$-acyl, $C_1$-$C_{18}$-halogenalkyl or cyano.

Triphenylmethane cations which are furthermore suitable are those of the formula

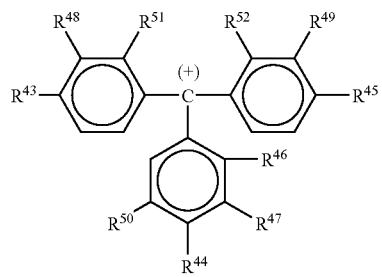

in which $R^{43}$ and $R^{45}$ are identical or different and denote —$NH_2$, a mono- or dialkylamino group, the alkyl groups of which have 1 to 4, preferably 1 or 2, carbon atoms, a mono- or di-omega-hydroxyalkylamino group, the alkyl groups of which have 2 to 4, preferably 2, carbon atoms, an optionally N—$(C_1$-$C_4)$alkyl-substituted phenyl- or phenalkylamino group, the alkyl of which has 1 to 4, preferably 1 or 2, carbon atoms and the phenyl nucleus of which can carry one or two of the radicals, methyl, ethyl, methoxy, ethoxy and sulfo.

$R^{44}$ is hydrogen or has one of the meanings given for $R^{43}$ and $R^{45}$, $R^{46}$ and $R^{47}$ denote hydrogen, halogen, preferably chlorine, or a sulfonic acid group, or $R^{46}$ forms a fused-on phenyl ring together with $R^{47}$, $R^{48}$, $R^{49}$, $R^{51}$ and $R^{52}$ each denote hydrogen or an alkyl radical having 1 or 2 carbon atoms, preferably methyl and $R^{50}$ is hydrogen or halogen, preferably chlorine.

Phosphonium and thionium cations which are furthermore suitable are those of the formulae (t) and (u)

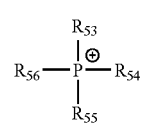
(t)

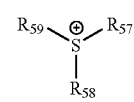
(u)

in which $R_{53}$ to $R_{59}$ independently of one another are $C_1$-$C_{18}$-alkyl, $C_2$-$C_{18}$-alkenyl, $C_1$-$C_{18}$-alkoxy, $C_1$-$C_{18}$-hydroxyalkyl, $(C_1$-$C_8)$alkylene-$(C_6$-$C_{10})$aryl, for example benzyl, alkyleneheteroaryl, $C_6$-$C_{10}$-aryl or heteroaryl, for example pyridinyl.

Fluorinated ammonium ions of the formula (x)

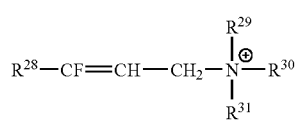
(x)

in which
$R^{28}$ denotes perfluorinated alkyl having 5 to 11 carbon atoms and
$R^{29}$, $R^{30}$ and $R^{31}$ are identical or different and denote alkyl having 1 to 5 carbon atoms, preferably 1 or 2 carbon atoms, are particularly preferred.

The structured silicates containing a low molecular weight organic cation can be prepared by bringing together one or more naturally occurring or synthetic structured silicates with a salt containing the low molecular weight organic cation, for example the corresponding chloride, bromide, iodide or methyl-sulfate, in aqueous suspension, expediently at a pH of between 0 and 14, preferably between 1 and 13, expediently at a temperature of 0 to 160° C., preferably 5 to 140° C., expediently under a pressure of 1 to 20 bar, for 5 minutes to 48 hours, preferably 10 minutes to 24 hours, in a molar ratio of organic cation: silicate of 1:100 to 10:1, preferably 1:20 to 3:1. It is advantageous to predisperse the structured silicate in water for between ½ and 48 hours, preferably between 1 and 24 hours, for example at a temperature of 5 to 100° C. It is furthermore advantageous to adjust the salt of the organic cation and/or the aqueous suspension of the structured silicate(s) to a pH of between 1 and 12, preferably 5 and 10, before the reaction in an aqueous medium.

A salt-like structure silicate in which the silicate is hectorite, beidellite, illite, muscovite, xantophyllite, margarite, sepiolite, saponite, mica, feldspar, nontronite, montmorillonite, smectite, bentonite, faujasite, zeolite A, X or Y, permutite, sasil or a combination thereof; and the cation is an ion of the formula (x) described above is novel and the present invention likewise relates to it. These novel compounds can be prepared as described above. These compounds can surprisingly show a charge assistant effect in the medium employed, in particular can achieve an assisting anti-offset action (better detachment of the toner from moving parts of the printing machinery which come into contact with the toner, for example photoconductors, deflection rollers).

The salts, used according to the invention, of ionic structured silicates can be matched accurately to the particular resin/toner system. Another technical advantage of these compounds is that they are inert toward the various binder systems and can thus be employed for diverse uses, it being of particular importance that they are not dissolved in the polymer matrix but are present as small, very finely divided solids. They furthermore show high and usually constant charge control properties and good heat stabilities. The structured silicates employed according to the invention are furthermore free-flowing and have a good dispersibility.

Dispersion means the distribution of one substance in another, in the sense of the invention the distribution of a charge control agent in the toner binder, powder coating binder or electret material.

It is known that crystalline substances in their coarsest form exist as agglomerates. To achieve a homogeneous distribution in the binder, these must be divided into smaller aggregates or ideally into primary particles by the dispersing operation. The charge control agent particles which exist after the dispersing in the binder should be smaller than 1 μm, preferably smaller than 0.5 μm, a narrow particle size distribution being of advantage. Action ranges which are optimum, depending on the substance, are found for the particle size, defined by the $d_{50}$ value. Thus, for example, coarse particles (1 mm) sometimes cannot even be dispersed at all or can be dispersed only with a considerable expenditure of time and energy, while very fine particles in the submicron range present an increased safety risk, such as the possibility of dust explosion.

The particle size and shape is established and modified either by the synthesis and/or aftertreatment. The property required is often only possible by controlled aftertreatment, such as grinding and/or drying. Various grinding techniques are suitable for this. Air jet mills, cutting mills, hammer mills, bead mills and impact mills, for example, are advantageous.

The binder systems mentioned in the present invention are typically hydrophobic materials. High water contents of the charge control agent can either oppose wetting or promote dispersing (flushing). The practicable moisture content is therefore substance-specific.

The compounds according to the invention are characterized by the following chemical physical properties:

The water content, determined by the Karl-Fischer method, is between 0.001% and 30%, preferably between 0.01 and 25%, and particularly preferably between 0.1 and 15%, it being possible for the water to be adsorbed and/or bonded, and for the content thereof to be adjusted by the action of heat up to 200° C. and vacuum down to $10^{-8}$ mmHg or by addition of water or storage under defined atmospheric humidity conditions.

Surprisingly, the compounds according to the invention which contain one or more organic cations defined above show no particularly increased $H_2O$ content (Karl-Fischer method) after storage at 90% relative atmospheric humidity and 25° C. in a climatic test cabinet for 48 hours, while the analogous structured silicates with metal cations show significantly higher $H_2O$ contents, sometimes several times that before the climatic storage.

The particle size, determined by means of light microscopy evaluation or laser light diffraction as defined by the $d_{50}$ value, is between 0.01 μm and 1000 μm, preferably between 0.1 and 500 μm, and very particularly preferably between 0.5 and 400 μm. It is particularly advantageous if a narrow particle size results from the grinding. A range Δ ($d_{95}$–$d_{50}$) of less than 500 μm, in particular less than 400 μm, is preferred.

The conductivity of the 5% strength aqueous dispersion is between 0.001 and 2000 mS, preferably between 0.01 and 100 mS. The compounds according to the invention contain both crystalline and amorphous contents.

The compounds used according to the invention, when incorporated into a toner binder, show a heat stability up to 200° C. (no discoloration) in a thermal gradient test (Kofler test).

In electrokinetic surface potential determination by means of SCD (streaming current detection), the compounds according to the invention with the organic cations defined above surprisingly show significantly lower surface potentials (positive or negative sign) than the corresponding structured silicates with metal cations. On titration of these compounds with corresponding surface-active reagents to the zero point of the surface potential (SCD monitoring of the titration), significantly more surface-active reagent is needed for the compounds with metal cations than for the corresponding structured silicates with organic cations. This indicates a high stability of the salt bond between the structured silicate and organic cation.

The salts, employed according to the invention, of ionic structured silicates can also be combined with further charge control agents with a positive or negative control in order to achieve good charging possibilities in use, the total concentration of the charge control agents expediently being between 0.01 and 50% by weight, preferably between 0.05 and 20% by weight, particularly preferably between 0.1 and 5% by weight, based on the total weight of the electrophotographic toner, developer, powder or powder coating.

Possible further charge control agents are, for example:
triphenylmethanes; ammonium and immonium compounds, iminium compounds; fluorinated ammonium and fluorinated immonium compounds, biscationic acid amides; polymeric ammonium compounds; diallylammonium compounds; arylsulfide derivatives, phenol derivatives; phosphonium compounds and fluorinated phosphonium compounds; calix(n)arenes, oligosaccharides linked in cyclic form (cyclodextrins) and derivatives thereof, in particular boron ester derivatives, interpolyelectrolyte complexes (IPECs); polyester salts; metal complex compounds, in particular salicylate-metal complexes and salicylate-nonmetal complexes, hydroxycarboxylic acid-metal complexes and hydroxycarboxylic acid-nonmetal complexes, benzimidazolones; azines, thiazines or oxazines which are listed in the Colour Index as pigments, solvent dyes, basic dyes or acid dyes.

The charge control agents mentioned below, which can be combined individually or in combination with one another with the salts of the ionic structured silicates, are particularly preferred:
triphenylmethanes, as described, for example, in U.S. Pat. No. 5,051,585; ammonium and immonium compounds, as described, for example, in U.S. Pat. No. 5,015,676; fluorinated ammonium and fluorinated immonium compounds, as described, for example, in U.S. Pat. No. 5,069,994; biscationic acid amides, as described, for example, in WO 91/10172; diallylammonium compounds, as described, for example, in DE-A-4 142 541, DE-A-4 029 652 or DE-A-4 103 610;

arylsulfide derivatives, as described, for example in DE-A-4 031 705; phenol derivatives, as described, for example, in EP-A-0 258 651; phosphonium compounds and fluorinated phosphonium compounds, as described, for example, in U.S. Pat. No. 5,021,473 and U.S. Pat. No. 5,147,748; calix(n) arenes, as described, for example, in EP-A-0 385 580; benzimidazolones, as described, for example, in EP-A-0 347 695; oligosaccharides linked in cyclic form, as described, for example, in DE-A-4 418 842; polyester salts, as described, for example, in DE-A-4 332 170;

cyclooligosaccharide compounds, as described, for example, in DE-A-197 11 260;

inter-polyelectrolyte complexes, as described, for example, in DE-A-197 32 995.

Surface-active ionic compounds and so-called metal soaps are furthermore suitable, especially for liquid toners.

Alkylated arylsulfonates, such as barium petronates, calcium petronates, barium dinonylnaphthalene sulfonates (basic and neutral), calcium dinonylsulfonate or dodecylbenzene sulfonic acid Na salt, and polyisobutylenesuccinimides (Chevrons OLOA® 1200) are particularly suitable.

Soylecithin and N-vinylpyrrolidone polymers are furthermore suitable. Sodium salts of phosphated mono- and diglycerides with saturated and unsaturated substituents, AB di-block copolymers of A: polymers of 2-(N;N)dimethylaminoethyl methacrylate quaternized with methyl p-toluenesulfonate and B: poly-2-ethylhexyl methacrylate are furthermore suitable.

Di- and trivalent carboxylates, in particular aluminum tristearate, barium stearate, chromium stearate, magnesium octoate, calcium stearate, iron naphthalate and zinc naphthalate are furthermore suitable, especially in liquid toners.

Chelating charge control agents (EP 0 636 945 A1), metallic (ionic) compounds (EP 0 778 501 A1), phosphate metal salts, as described in JA 9 (1997)-106107, are furthermore suitable. Azines of the following Colour Index Numbers: C.I. Solvent Black 5, 5:1, 5:2, 7, 31 and 50; C.I. Pigment Black 1, C.I. Basic Red 2 and C.I. Basic Black 1 and 2 are furthermore suitable.

The structured silicates used according to the invention are incorporated homogeneously, for example by extrusion or kneading, bead grinding or with an ULTRATURRAX® (high-speed stirrer) into the binder of the particular toner, developer, coating, powder coating, electret material or polymer to be separated electrostatically individually or in combination with one another or with further above mentioned charge control agents in a concentration of 0.01 to 50% by weight, preferably 0.05 to 20% by weight, particularly preferably 0.1 to 5.0% by weight, based on the total mixture. The compounds employed according to the invention can be added here as dried and ground powders, dispersions or solutions, presscakes, masterbatches, preparations, mixed pastes, as compounds absorbed from aqueous or non-aqueous solution onto suitable carriers, such as, for example, silica gel, or mixed with such carriers, $TiO_2$, $Al_2O_3$ or carbon black, or in another form. The compounds used according to the invention can in principle also be added as early as during the preparation of the particular binders, that is to say in the course of polymerization, polyaddition or polycondensation thereof.

To prepare electrophotographic color toners, coloring agents, such as organic color pigments, inorganic pigments or dyestuffs, are added. The organic color pigments can be pigments from the group consisting of azo pigments or polycyclic pigments or mixed crystals (solid solutions) of such pigments.

Preferred blue and/or green pigments are copper phthalocyanines, such as C.I. Pigment Blue 15, 15:1, 15:2, 15:3, 15:4, 15:6, P. Blue 16 (metal-free phthalocyanine), or phthalocyanines with aluminum, nickel, iron or vanadium as the central atom, and furthermore triarylcarbonium pigments, such as Pigment Blue 1, 2, 9, 10, 14, 62, 68, Pigment Green 1, 4, 7, 45; orange pigments, such as, for example, P.O. 5, 62, 36, 34, 13, 43, 71; yellow pigments, such as, for example, P.Y. 12, 13, 17, 83, 93, 122, 155, 180, 174, 185, 97; red pigments, such as, for example, P.R. 48, 57, 122, 146, 149, 184, 202, 207, 209, 254, 255, 269, 270, 272; violet pigments, such as P.V. 1, 19, carbon black, iron/manganese oxides; and furthermore mixed crystals of C.I. Pigment Violet 19 and C.I. Pigment Red 122. The mixtures can be prepared in the form of the powders, by mixing presscakes, spray-dried presscakes, masterbatches and by dispersing (extrusion, kneading, roll mill processes, bead mills, ULTRATUR-RAX®) in the presence of a carrier material in solid or liquid form (in water-based and non-aqueous inks) and by flushing in the presence of a carrier material.

If the coloring agent is employed with high water or solvent contents (>5%), mixing can also proceed with assistance in the presence of elevated temperatures and by vacuum. The flushing operation can proceed in the presence or absence of organic solvents and of waxes.

Mixtures with organic dyestuffs are suitable in particular for increasing the brilliance, but also for adjusting the color shade. Preferred such dyestuffs which are to be mentioned are:

water-soluble dyestuffs, such as, for example, direct, reactive and acid dyes, and solvent-soluble dyestuffs, such as, for example, solvent dyes, disperse dyes and vat dyes. Examples which may be mentioned are: C.I. Reactive Yellow 37, Acid Yellow 23, Reactive Red 23, 180, Acid Red 52, Reactive Blue 19, 21, Acid Blue 9, Direct Blue 199, Solvent Yellow 14, 16, 25, 56, 62, 64, 79, 81, 82, 83, 83:1, 93, 98, 133, 162, 174, Solvent Red 8, 19, 24, 49, 89, 90, 91, 92, 109, 118, 119, 122, 124, 127, 135, 160, 195, 212, 215, Solvent Blue 44, 45, Solvent Orange 41, 60, 63, Disperse Yellow 64, Vat Red 41, Solvent Black 45, 27.

Dyestuffs and pigments with fluorescent properties, such as LUMINOLE® (Riedel-de Haen) can also be employed, for example to prepare falsification-proof toners.

Inorganic pigments, such as, for example $TiO_2$ or $BaSO_4$, are used in mixtures for brightening. Mixtures with effect pigments, such as, for example, pearlescent pigments, $Fe_2O_3$ pigments (PALIOCHROME®) and pigments based on cholesteric polymers, which produce different color impressions depending on the angle of observation, are furthermore suitable.

The present invention also relates to an electrophotographic toner, powder or powder coating comprising 30 to 99.99% by weight, preferably 40 to 99.5% by weight, of a customary binder, for example a styrene, styrene/acrylate, styrene/butadiene, acrylate, urethane, acrylic, polyester or epoxy resin, or a combination of the last two, 0.01 to 50% by weight, preferably 0.05 to 20% by weight, particularly preferably 0.1 to 5% by weight, of at least one salt of ionic structured silicate and optionally 0.001 to 50% by weight, preferably 0.05 to 20% by weight, of a coloring agent, in each case based on the total weight of the electrophotographic toner, powder or powder coating.

The compounds described according to the invention can furthermore be applied to "free-flow agents" as an additional charge control element in suspended form or in a dry mixture. The compounds described according to the invention can also be employed for a "carrier coating".

EXAMPLES

In the following examples, parts denote parts by weight and percent denotes percentage by weight.

Preparation Example 1

10 g of bentonite (pH 7-12) are dispersed in 300 ml of deionized water by means of stirring for 16 hours at 20° C. The suspension is then adjusted to a pH of between 1.5 and 8 by means of dilute sulfuric acid, and thereafter 5.3 g of a 77% strength aqueous distearyldimethylammonium chloride solution (DSDMAC) are added to the bentonite suspension. The reaction mixture is subsequently stirred at 60° C. for 4 hours and filtered with suction and the residue is rinsed several times with deionized water and then dried at 60° C. in vacuo.

Characterization:

| | White to pale gray powder |
|---|---|
| DTA: | no decomposition up to 190° C. |
| pH: | 8.4 |
| Conductivity: | 0.062 mS/cm |
| Residual moisture content: | 1.4% (Karl-Fischer Titration) |
| tan δ (1 kHz): | 0.78 |
| Ω cm: | $5 \cdot 10^8$ |
| Crystallinity: | >70% (X-ray diffraction); numerous reflection peaks between 2 Theta 5 and 55° (main peaks: 3.5°; 6.6°; 19.8°; 23.7°; 24.4°; 27.7°; 35.0°; 38.3°; 54.0°). |
| Solubilities: | insoluble in water, ethanol, acetone, n-hexane (<10 mg/l). |

Preparation Example 2

10 g of a magnesium hydrosilicate (OPTIGEL® SH, "Hectorite") are dispersed in 400 ml of deionized water at room temperature for 2 hours.

6.0 g of an 80% strength aqueous distearylmethylbenzyl-/distearyldimethylammonium chloride mixture (DSMB/DSDMAC) are then added and the reaction mixture is stirred at 80-100° C. for 30 minutes. The precipitate is filtered off with suction, washed several times with deionized water and dried at 60° C. in vacuo.

Preparation Examples 3 to 28

| No. | Preparation according to example | Structured silicate used | Organic cation |
|---|---|---|---|
| 3 | 2 | Hectorite | Fluorinated quat |
| 4 | 1 | Montmorillonite | Fluorinated quat |
| 5 | 1 | Acid bentonite | DSMB/DSDMAC |
| 6 | 1 | Acid bentonite | Fluorinated quat |
| 7 | 1 | Magnesium hydrosilicate | Protonated prim. amine ($C_{16/18}$) |
| 8 | 1 | Magnesium hydrosilicate | Protonated primary amine ($C_8$) |
| 9 | 1 | Alkaline bentonite | Cetyltrimethylammonium |
| 10 | 1 | Alkaline bentonite | Coconut alkyldimethylbenzyl-ammonium |
| 11 | 1 | Alkaline bentonite | Didecyldimethylammonium |
| 12 | 1 | Alkaline bentonite | Dioctyldimethylammonium |
| 13 | 1 | Alkaline bentonite | Fluorinated quat |
| 14 | 1 | Alkaline bentonite | Triphenylmethane cation |
| 15 | 1 | Alkaline bentonite | Diallyldimethyl-ammonium |
| 16 | 1 | Alkaline bentonite | Tetrapropylammonium |
| 17 | 1 | Alkaline bentonite | $(R)_3N-CH_3$ R = $(CH_2)_2O-CO(CH_2)_{11-21}CH_3$ |
| 18 | 1 | Alkaline bentonite | $C_{12}/C_{14}$-Alkyldimethylbetaine |
| 19 | 1 | Alkaline bentonite | Sulfinato-Sulfobetaine |
| 20 | 1 | Alkaline bentonite | Trimethyltriazacyclononanium |
| 21 | 1 | Alkaline bentonite | Zn-salicylate 1:1 complex |
| 22 | 1 | Alkaline bentonite | Cetylpyridinium |
| 23 | 1 | Aqueous bentonite | Distearyldimethylammonium |
| 24 | 1 | Kaolinite | Distearyldimethylammonium |
| 25 | 1 | Magnesium hydrosilicate | Distearyldimethylammonium |
| 26 | 1 | Alkaline bentonite | Methylene blue |
| 27 | 1 | dto. | 1-Methyl-1-stearylamidoethyl-2-stearylimidazolinium |
| 28 | 1 | dto. | Methyl-bis(stearylamidoethyl)-poly(ethylenoxid)ammonium |

| Fluorinated quat: | $R - CF = CH - CH_2 - N^+Et_2Me$ R = $C_5F_{11}$ to $C_{11}F_{23}$ |
|---|---|

Characterization of Preparation Example 11

| | White to pale gray powder |
|---|---|
| DTA: | no decomposition up to 200° C. |
| pH: | 8.7 |
| Conductivity: | 0.09 mS/cm |
| Residual moisture content: | 1.0% (Karl Fischer Titration) |
| SCD: | U = −150 mV (10 ml of 0.5% strength suspension); titration to U = 0 mV with 0.1 ml of $10^{-3}$ M Polydadmac solution |
| tan δ (1 kHz): | 2.7 |
| Ω cm: | $6 \cdot 10^7$ |
| Crystallinity: | >70% (X-ray diffraction); numerous reflection peaks between 2 Theta 5 and 55° (main peaks: 4.9°; 9.7°; 19.8°; 23.6°; 24.9°; 29.9°; 35.0°; 45.3°; 54.0°) |
| Particle size distribution: | $d_{50}$ = 26 μm, $d_{95}$ = 213 μm (laser light diffraction) |
| BET: | 23.4 m$^2$/g |
| Solubilities: | insoluble in water, ethanol, acetone, n-hexane (<10 mg/l). |

Characterization of Preparation Example 13

| | White to pale gray powder |
|---|---|
| DTA: | no decomposition up to 250° C. |
| pH: | 5.0 |
| Conductivity: | 0.20 mS/cm |
| Residual moisture content: | 1.6% (Karl Fischer Titration) |
| SCD: | U = −210 mV (10 ml of 0.5% strength suspension); titration to U = 0 with 0.22 ml of $10^{-3}$ M Polydadmac solution |
| tan δ (1 kHz): | 1.3 |
| Ω cm: | $6 \cdot 10^8$ |
| Crystallinity: | >70% (X-ray diffraction); numerous reflection peaks between 2 Theta 5 and 55° (main peaks: 6.0° ; 18.3°; 19.8°; 24.5°; 30.7°; 34.9°; 38.3°, 43.4°, 54.0°) |
| Particle size distribution: | $d_{50}$ = 90 μm, $d_{95}$ = 390 μm (laser light diffraction) |
| BET: | 17.8 m²/g |
| Solubilities: | insoluble in water, ethanol, acetone, n-hexane (<10 mg/l). |

Use Examples

Use Example 1

1 part of the compound from Preparation Example 1 is incorporated homogeneously into 99 parts of a toner binder (styrene/acrylate copolymer 60:40 DIALEC® S 309) in the course of 30 minutes by means of a kneader. The mixture is subsequently ground on a laboratory universal mill and then classified on a centrifugal sifter. The desired particle fraction (4 to 25 μm) is activated with a carrier with comprises magnetite particles of size 50 to 200 μm coated with styrene/methacrylate copolymer (90:10).

Use Example 2

The procedure is as in Use Example 1, a polyester resin based on bisphenol A (ALMACRYL® T 500) being used instead of the styrene/acrylate copolymer and ferrite particles of size 50-200 μm coated with silicone being used as the carrier.

The measurement is carried out on a customary q/m measuring stand. By using a sieve with a mesh width of 45 μm, it is ensured that no carrier is carried along with the blown-out toner. The measurements are carried out at about 50% relative atmospheric humidity. The following q/m values [μC/g] are measured, depending on the duration of the activation.

| | Use example | |
|---|---|---|
| | 2 | 1 |
| Duration of the activation | Charging q/m [μC/g] | |
| 5 minutes | −22 | −20 |
| 10 minutes | −18 | −21 |
| 30 minutes | −13 | −18 |
| 2 hours | −11 | −9 |

Use Examples 3 to 37

The procedure is as in Use Example 1 or 2, the compounds listed below being employed instead of the compounds of Preparation Example 1.

| Exp. | Compound employed | Incorporated according to Use Example | q/m [μC/g] 5 min. | 10 min. | 30 min. | 2 Hrs. | 24 Hrs. |
|---|---|---|---|---|---|---|---|
| 3 | Magnesium hydrosilicate (® Optigel SH) | 1 | −6 | −6 | −8 | −8 | — |
| 4 | Acid bentonite | 2 | −9 | −8 | −5 | −4 | −3 |
| 5 | Acid bentonite | 1 | −4 | −7 | −10 | −9 | −12 |
| 6 | Montmorillonite K 10 | 2 | −8 | −6 | −4 | −1 | — |
| 7 | Montmorillonite K 10 | 1 | −4 | −6 | −7 | −6 | −6 |
| 8 | OPTIGEL ® WM | 1 | −1 | −2 | −2 | −3 | — |
| 9 | Kaolinite | 1 | ±0 | −1 | −1 | −2 | — |
| 10 | Alkaline bentonite | 1 | −7 | −10 | −10 | −19 | — |
| 11 | Preparation Example 2 | 1 | +4 | +7 | +12 | +18 | +21 |
| 12 | Preparation Example 3 | 1 | +2 | +7 | +13 | +14 | +16 |
| 13 | Preparation Example 3 | 2 | +3 | +4 | +3 | +2 | +1 |
| 14 | Preparation Example 4 | 1 | +1 | +3 | +8 | +9 | +10 |
| 15 | Preparation Example 5 | 1 | +1 | +5 | +10 | +17 | +21 |
| 16 | Preparation Example 6 | 1 | +2 | +6 | +10 | +12 | +10 |
| 17 | Hectorite + DSDMAC | 1 | +3 | +6 | +10 | +15 | +19 |
| 18 | Preparation Example 9 | 1 | −13 | −14 | −16 | −13 | — |
| 19 | Preparation Example 10 | 1 | −15 | −16 | −16 | −13 | — |
| 20 | Preparation Example 11 | 1 | −18 | −20 | −18 | −14 | — |
| 21 | Preparation Example 12 | 1 | −13 | −14 | −14 | −12 | — |
| 22 | Preparation Example 13 | 1 | −20 | −21 | −19 | −15 | — |
| 23 | Preparation Example 14 | 1 | −11 | −13 | −13 | −10 | — |
| 24 | Preparation Example 15 | 1 | −5 | −6 | −6 | −4 | — |
| 25 | Preparation Example 16 | 1 | −17 | −16 | −14 | −9 | — |
| 26 | Preparation Example 17 | 1 | −17 | −18 | −16 | −10 | — |
| 27 | Preparation Example 18 | 1 | −16 | −16 | −17 | −13 | — |
| 28 | Preparation Example 19 | 1 | −13 | 16 | −19 | −16 | — |
| 29 | Preparation Example 20 | 1 | −7 | −8 | −9 | −8 | — |

-continued

| Exp. | Compound employed | Incorporated according to Use Example | q/m [μC/g] | | | | |
|---|---|---|---|---|---|---|---|
| | | | 5 min. | 10 min. | 30 min. | 2 Hrs. | 24 Hrs. |
| 30 | Preparation Example 21 | 1 | −14 | −16 | −16 | −14 | |
| 31 | Preparation Example 22 | 1 | −13 | −17 | −18 | −15 | |
| 32 | Preparation Example 23 | 1 | −2 | −2 | −2 | −2 | |
| 33 | Preparation Example 24 | 1 | −1 | ±0 | ±0 | +2 | |
| 34 | Preparation Example 25 | 1 | +3 | +6 | +10 | +15 | +20 |
| 35 | Preparation Example 26 | 1 | −13 | −14 | −14 | −13 | |
| 36 | Preparation Example 27 | 1 | −15 | −16 | −17 | −17 | |
| 37 | Preparation Example 28 | 1 | −16 | −18 | −19 | −19 | |

Use Examples 38 to 40

The procedure is as in Use Example 1, either 0.5, 2 or 3 parts of the compound from Preparation Example 1 being employed instead of 1 part.

Use Examples 41 and 42

The procedure is as in Use Example 2, 2 or 3 parts of the compound from Preparation Example 1 being employed instead of 1 part.

| Exp. No. | Parts | q/m [μC/g] | | | | |
|---|---|---|---|---|---|---|
| | | 5 minutes | 10 minutes | 30 minutes | 2 hours | 24 hours |
| 38 | 0.5 | −17 | −19 | −15 | −6 | |
| 39 | 2 | −32 | −30 | −21 | −6 | |
| 40 | 3 | −36 | −31 | −23 | −14 | |
| 41 | 2 | −28 | −25 | −23 | −21 | −19 |
| 42 | 3 | −32 | −26 | −24 | −23 | −21 |

Use Examples 43 and 44

The procedure is as in Use Example 1, 1 or 5 parts of a coloring agent having an electrostatically positive intrinsic effect (C.I. Solvent Blue 125, see Comparison Example A) also being incorporated in addition to the 1 part of the compound from Preparation Example 1.

| No. | Parts of coloring agent | q/m [μC/g] | | | | |
|---|---|---|---|---|---|---|
| | | 5 minutes | 10 minutes | 30 minutes | 2 hours | 24 hours |
| 43 | 1 | −17 | −15 | −11 | −7 | −5 |
| 44 | 5 | −5 | −4 | −3 | −4 | −3 |

Use Examples 45 to 53

The procedure is as in Use Examples 1, 38 and 39, 5 parts of an organic pigment (carbon block MOGUL® L, Cabot; Toner Magenta EO2, Clariant (C.I. P. Red 122); Toner Yellow HG, Clariant (C.I. P. Yellow 180)) additionally also being incorporated.

| No. | Parts of compound from Preparation Example 1 | Organic pigment | q/m [μC/g] | | | | |
|---|---|---|---|---|---|---|---|
| | | | 5 min. | 10 min. | 30 min. | 2 hrs. | 24 hrs. |
| 45 | 0.5 | Toner Magenta EO2 | −16 | −14 | −10 | −8 | −5 |
| 46 | 1 | Toner Magenta EO2 | −21 | −17 | −14 | −10 | −3 |
| 47 | 2 | Toner Magenta EO2 | −22 | −21 | −16 | −7 | −5 |
| 48 | 0.5 | Toner Yellow HG | −21 | −21 | −19 | −13 | −8 |
| 49 | 1 | Toner Yellow HG | −24 | −24 | −21 | −11 | −6 |
| 50 | 2 | Toner Yellow HG | −29 | −26 | −22 | −13 | −8 |
| 51 | 0.5 | Carbon black | −15 | −15 | −12 | −8 | −6 |
| 52 | 1 | Carbon black | −20 | −18 | −15 | −13 | −9 |
| 53 | 2 | Carbon black | −22 | −20 | −16 | −12 | −8 |

Comparison Example A

The procedure is as in Use Example 43, 1 part of C.I. Solvent Blue 125 but no charge control agent according to the invention being incorporated.

| Duration of activation | Charging q/m [μC/g] |
|---|---|
| 5 minutes | ±0 |
| 10 minutes | +1 |
| 30 minutes | +3 |
| 120 minutes | +10 |
| 24 hours | +29 |

The pronounced positive triboelectric intrinsic effect of the blue coloring agent is clearly detectable.

Use Example 54

1 part of the compound from Use Example 1 was incorporated homogeneously into 99 parts of a powder coating binder (CRYLCOAT® 430), as described in the Use Examples mentioned above. Tribo-spraying of the powder (coatings) was carried out with a TRIBOSTAR® spray apparatus from Intec (Dortmund) with a standard spray tube and a star inner rod at maximum powder throughput with a spray pressure of 3 and 5 bar. The current intensity resulting from the electrostatic charging of the powder coating or powder was indicated in μA. The deposition rate was then determined in % by the difference in weight of the powder coating sprayed and that deposited.

| Pressure [bar] | Current [μA] | Deposition rate [%] |
|---|---|---|
| 3 | 3.9 | 40 |
| 5 | 5.3 | 48 |

The invention claimed is:

1. A method of imparting, controlling or improving the charge of an electrophotographic toner or developer, or an electret material, consisting of adding only a structured silicate salt, wherein the cation is a low molecular weight, nonpolymeric ammonium ion or a combination of a low molecular weight, nonpolymeric ammonium ion with $NH_4^+$, $H_3O^+$, an alkali metal, an alkaline earth metal, an earth metal or with a transition metal and the anion is an island, cyclic, group, chain, ribbon, laminar or matrix silicate or a combination thereof to a binder of an electrophotographic toner or developer or of an electret material, wherein the low molecular weight, nonpolymeric ammonium ion is selected from one of the formulas (a) through (j)

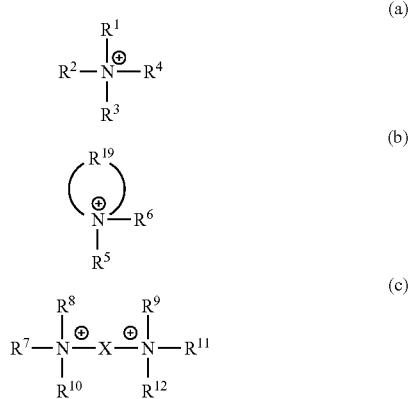

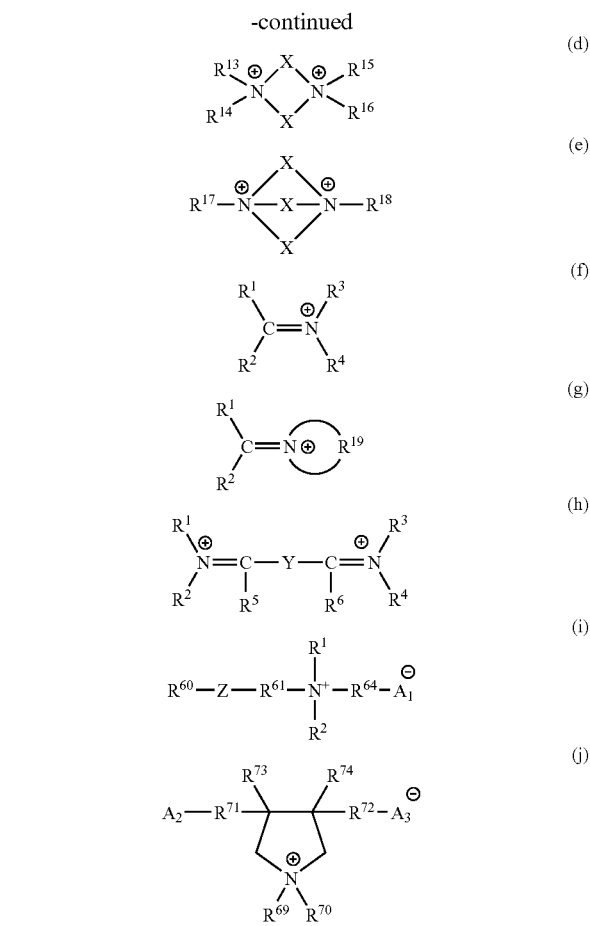

in which $R^1$ to $R^{18}$ are identical or different and represent hydrogen, CN, $(CH_2)_{1-18}CN$, halogen, branched or unbranched $C_1$-$C_{32}$-alkyl, mono- or polyunsaturated $C_2$-$C_{32}$-alkenyl, $C_1$-$C_{22}$-alkoxy, $C_1$-$C_{22}$-hydroxyalkyl, $C_1$-$C_{22}$-halogenoalkyl, $C_2$-$C_{22}$-halogenoalkenyl, $C_1$-$C_{22}$-aminoalkyl, $(C_1$-$C_{12})$-trialkyl-ammonium-$(C_1$-$C_{22})$-alkyl; $(C_1$-$C_{22})$-alkylene-(C=O)O—$(C_1$-$C_{32})$alkyl, $(C_1$-$C_{22})$-alkylene-(C=O)O-aryl, $(C_1$-$C_{22})$-alkylene-(C=O)NH—$(C_1$-$C_{32})$alkyl, $(C_1$-$C_{22})$-alkylene-(C=O)NH-aryl, $(C_1$-$C_{22})$-alkylene-O(C=O)—$(C_1$-$C_{32})$alkyl, $(C_1$-$C_{22})$-alkylene-O(CO)aryl, $(C_1$-$C_{22})$-alkylene-NH(C=O)—$(C_1$-$C_{32})$alkyl, or $(C_1$-$C_{22})$-alkylene-NHCO-aryl, wherein

are optionally inserted into the acid ester or acid amide bonds;

$[(C_1$-$C_{12})$-alkylene-O—]—H; aryl, $(C_1$-$C_{18})$-alkylene-aryl; —(O—SiR'$_2$)—O—SiR'$_3$, in which R' has the meaning $C_1$-$C_{12}$-alkyl, phenyl, benzyl or $C_1$-$C_{12}$-alkoxy; heterocyclyl, or $C_1$-$C_{18}$-alkylene-heterocyclyl, wherein the aryl and heterocyclyl radicals are optionally mono- or polysubstituted on carbon atoms or heteroatoms by $C_1$-$C_{12}$-alkyl, $C_1$-$C_4$-alkenyl, $C_1$-$C_4$-alkoxy, hydroxy-$(C_1$-$C_4)$alkyl, amino-$(C_1$-$C_4)$alkyl, $C_1$-$C_4$-alkylimino, carboxyl, hydroxyl, amino, nitro, cyano, halogen, $C_1$-$C_{12}$-acyl, $C_1$-$C_4$-halogenalkyl, $C_1$-$C_4$-alkylcarbonyl, $C_1$-$C_4$-alkylcarbonyloxy, $C_1$-$C_4$-alkoxycarbonyl, $C_1$-$C_4$-alkylaminocarbonyl, $C_1$-$C_4$-alkylcarbonylimino, $C_6$-$C_{10}$-arylcarbonyl, aminocarbonyl, aminosulfonyl, $C_1$-$C_4$-alkylaminosulfonyl, phenyl, naphthyl, or heteroaryl;

$R^{19}$ represents $C_4$-$C_{11}$-alkylene, —$(C_2H_4$—O—$)_{1-17}$—$(CH_2)_{1-2}$— or —$(C_2H_4$—NR—$)_{1-17}$—$(CH_2)_{1-2}$—, in which R is hydrogen or $C_1$-$C_{12}$-alkyl;

X has the meaning of Y, or —CO—$CH_2$—CO—,

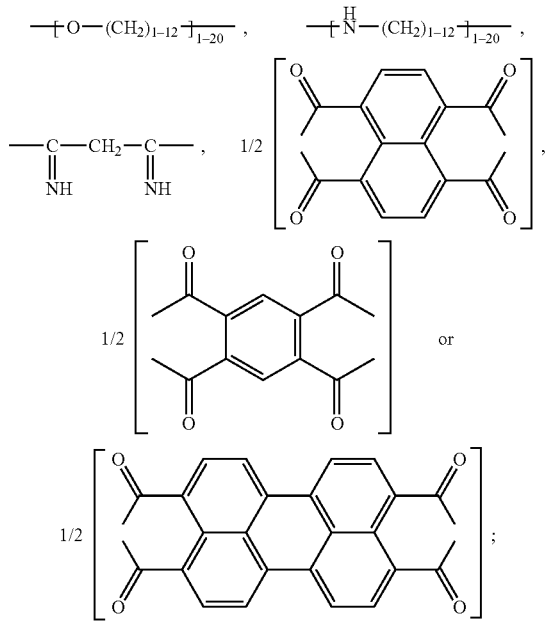

Y has the meaning

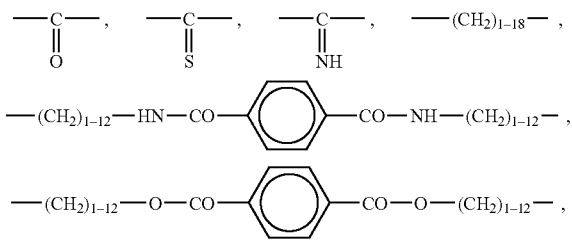

or o-, p-, m-$(C_6$-$C_{14})$-arylene or $(C_4$-$C_{14})$-heteroarylene with 1, 2, 3 or 4 heteroatoms from the group consisting of N, O, S and a combination thereof;

$R^{60}$ represents $C_1$-$C_{32}$-acyl, $C_1$-$C_{22}$-alkyl, $C_2$-$C_{22}$-alkenyl, $C_1$-$C_{18}$-alkylene-$C_6$-$C_{10}$-aryl, $C_1$-$C_{22}$-alkylene-heterocyclyl, $C_6$-$C_{10}$-aryl or $(C_4$-$C_{14})$-heteroaryl with 1, 2, 3 or 4 heteroatoms from the group consisting of N, O, S, and a combination thereof;

$R^{61}$ and $R^{64}$ represent —$(CH_2)_{1-18}$—, $C_1$-$C_{12}$-alkylene-$C_6$-$C_{10}$-arylene, $C_6$-$C_{10}$-arylene, or $C_0$-$C_{12}$-alkylene-heterocyclyl;

Z represents —NH— or —O—;

$A_1^-$ and $A_3^-$ represent —$COO^-$, —$SO_3^-$, —$OSO_3^-$, —$SO_2^-$, —$COS^-$ or —$CS_2^-$;

$A_2$ represents —$SO_2Na$, —$SO_3Na$, —$SO_2H$, —$SO_3H$ or hydrogen;

$R^{69}$ and $R^{70}$ independently of one another represent hydrogen, $C_1$-$C_{32}$-alkyl, in which the alkyl chain optionally contain one or more of the groups selected from the group consisting of —NH—CO—, —CO—NH—, —CO—O—, and —O—CO—; $C_1$-$C_{18}$-alkylene-aryl, $C_0$-$C_{18}$-alkylene-heterocyclyl, $C_1$-$C_{18}$-hydroxyalkyl, $C_1$-$C_{18}$-halogenoalkyl, aryl, —$(CH_2)_3$—$SO_3^-$,

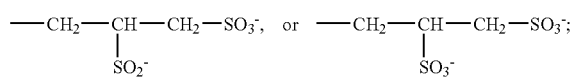

$R^{71}$ and $R^{72}$ represent —$(CH_2)_{1-12}$—; and $R^{73}$ and $R^{74}$ represent hydrogen or $C_1$-$C_{22}$-alkyl.

2. The method as claimed in claim 1, wherein $R^1$ to $R^{18}$ is hydrogen, CN, $CH_2$—CN, $CF_3$, $C_1$-$C_{22}$-alkyl, $C_2$-$C_{18}$-alkenyl, $C_1$-$C_{18}$-alkoxy, $C_1$-$C_{18}$-hydroxy-alkyl, $C_1$-$C_{18}$-halogenoalkyl, $C_2$-$C_{18}$-halogenoalkenyl, $C_1$-$C_{18}$-aminoalkyl, $(C_1$-$C_6)$-trialkylammonium-$(C_1$-$C_{18})$-alkyl, $(C_1$-$C_{18})$-alkylene-O(C=O)—$(C_1$-$C_{22})$alkyl, $(C_1$-$C_{18})$-alkylene-O(C=O)-phenyl, $(C_1$-$C_{18})$-alkylene-NHCO—$(C_1$-$C_{22})$alkyl, $(C_1$-$C_{18})$-alkylene-NHCO-phenyl, $(C_1$-$C_{18})$-alkylene-(C=O)O—$(C_1$-$C_{22})$alkyl, $(C_1$-$C_{18})$-alkylene-(C=O)O-phenyl, $(C_1$-$C_{18})$alkylene-(C=O)NH—$(C_1$-$C_{22})$alkyl, $(C_1$-$C_{18})$-alkylene-CONH-phenyl, benzyl, phenyl, naphthyl or $C_1$-$C_{12}$-alkylene-heterocyclyl;

$R^{19}$ denotes $C_4$-$C_5$-alkylene, —$(C_2H_4$—O$)_{1-9}$—$(CH_2)_{1-2}$— or —$(C_2N_4$—NH$)_{1-9}$—$(CH_2)_{1-2}$—;

$R^{60}$ denotes $C_1$-$C_{18}$-acyl, $C_1$-$C_{18}$-alkyl, $C_2$-$C_{18}$-alkenyl, $C_1$-$C_{12}$-alkylene-phenyl, $C_1$-$C_{18}$-alkylenepyridyl, phenyl or pyridyl;

$R^{61}$ and $R^{64}$ are —$(CH_2)_{1-12}$—, $C_1$-$C_8$-alkylene-phenylene, phenylene or $C_1$-$C_8$-alkylenepyridylene or -piperidylene;

$R^{71}$ and $R^{72}$ are —$(CH_2)_{1-8}$ and $R^{73}$ and $R^{74}$ are hydrogen or $(C_1$-$C_{18})$-alkyl.

3. The method according to claim 1, wherein the structured silicate salt is distearyldimethyl ammonium bentonite.

4. The method according to claim 1, wherein the structured silicate salt imparts either a positive or negative charge.

5. A method of imparting, controlling or improving the charge of an electrophotographic toner or developer, or an electret material, consisting of adding only a structured silicate salt, wherein the cation is a low molecular weight, nonpolymeric ammonium ion or a combination of a low molecular weight, nonpolymeric ammonium ion with $NH_4^+$, $H_3O^+$, an alkali metal, an alkaline earth metal, an earth metal or with a transition metal and the anion is an island, cyclic, group, chain, ribbon, laminar or matrix silicate or a combination thereof to a binder of an electrophotographic toner or developer or of an electret material, wherein the low molecular weight, nonpolymeric ammonium ion is an aliphatic or aromatic 5- to 12-membered heterocyclic radical with 1 to 4 atoms selected from the group consisting of N, O, S and a combination thereof, belonging to the rings.

6. The method as claimed in claim 5, wherein the heterocyclic radical is pyridinium, pyridazinium, pyrimidinium, pyrazinium, purinium, tetraazaporphyrinium, piperidinium, morpholinium, tetrazonium, triazacyclononanium or tetraaza-cyclododecanium.

* * * * *